United States Patent
Pasini et al.

(10) Patent No.: US 7,856,084 B2
(45) Date of Patent: Dec. 21, 2010

(54) METHOD FOR ACTIVATION OF AN EMITTER OF A COMPUTED TOMOGRAPHY SCANNER

(75) Inventors: Alessandro Pasini, Cesena (IT); Eros Nanni, Castel Guelfo Di Bologna (IT)

(73) Assignee: Cefla Societa' Cooperativa, Imola (IT)

( * ) Notice: Subject to any disclaimer, the term of this patent is extended or adjusted under 35 U.S.C. 154(b) by 218 days.

(21) Appl. No.: 12/051,688

(22) Filed: Mar. 19, 2008

(65) Prior Publication Data

US 2008/0232543 A1 Sep. 25, 2008

(30) Foreign Application Priority Data

Mar. 20, 2007 (EP) ................... 07425160

(51) Int. Cl.
*H05G 1/38* (2006.01)

(52) U.S. Cl. ............... 378/97; 378/16; 378/96; 378/108

(58) Field of Classification Search ............ 378/16, 378/19, 96, 98.8, 106, 108, 97
See application file for complete search history.

(56) References Cited

U.S. PATENT DOCUMENTS

| | | | |
|---|---|---|---|
| 5,949,811 A | 9/1999 | Baba et al. | |
| 6,490,337 B1 | 12/2002 | Nagaoka et al. | |
| 2001/0041832 A1 | 11/2001 | Hirai | |
| 2002/0085672 A1 | 7/2002 | Ganin et al. | |
| 2004/0247069 A1 | 12/2004 | Arai et al. | |

FOREIGN PATENT DOCUMENTS

WO 2006/090877 8/2006

*Primary Examiner*—Chih-Cheng G Kao
(74) *Attorney, Agent, or Firm*—Fish & Richardson P.C.

(57) ABSTRACT

In a computed tomography scanner having an emitter for emitting a beam of given radiation through an object to be analysed, a detector for receiving said beam after the beam itself has traversed the object, and a rotating arm, which supports the emitter and the detector and rotates the emitter and the detector about the object along a series of angular positions, there is generated a succession of first pulses, each of which activates the detector in one respective angular position, and a succession of second pulses for activating the emitter so that it will emit a dose of radiation in each angular position, associated to which is a respective dose of radiation in such a way as to pre-define a distribution of doses of radiation along the series of angular positions.

11 Claims, 2 Drawing Sheets

METHOD FOR ACTIVATION OF AN EMITTER OF A COMPUTED TOMOGRAPHY SCANNER

The present invention relates to a method for activation of an emitter of a computed tomography scanner.

In particular, the present invention finds advantageous, but not exclusive, application in computed tomography scanners used in the sector of dentistry, to which the ensuing description will make explicit reference, without this implying any loss of generality.

BACKGROUND OF THE INVENTION

Computed tomography scanners (CT scanners) used in the field of dentistry are of the cone-beam type (Cone-Beam Computed Tomography) and comprise an x-ray source-detector assembly designed to rotate about an area of analysis in which the head of a patient is positioned for acquiring volumetric tomographic data of one or both of the dental arches of the patient. The source-detector assembly comprises: a rotating support, constituted typically by a motor-driven arm so as to rotate about a horizontal axis traversing said area of analysis; an x-ray emitter, mounted on a first end of the arm for emitting a conical x-ray beam through the area of analysis; and an x-ray detector, mounted on the opposite end of the arm and facing the emitter for receiving the beam after it has traversed the area of analysis so as to be able to acquire a plurality of radiographies of the dental arches during a single rotation of the arm along an angular path of less than or equal to 360°.

The tomography scanner further comprises a control unit, connected to the source-detector assembly for controlling emission and reception of the beam in a way synchronous with rotation of the arm, and a processing unit, connected to the detector for receiving, storing, and processing the radiographies acquired for different angular positions of the rotating support so as to be able to reconstruct images of dental arches.

The radiation dose that the emitter must emit in order for the detector to be able to acquire a correct radiography depends upon the thickness of the bony parts that the x-ray beam has to traverse, and hence in general upon the dimensions of the skull of the patient. Before acquiring the radiographies, the emitter of the tomography scanner is adjusted for emitting a radiation dose adequate for the skull being examined, for example that of a child or an adult. The radiation dose required is determined via acquisition of one or two radiographies of the patient's head known as scout-views that precedes acquisition of the radiographies for reconstruction of the images.

The tomography scanner of the type mentioned above is hence used successfully for acquiring images of the complete dentition of the patient. In principle, said tomography scanner could be used also for acquiring images of a particular anatomical part located in any point of the patient's head, but the modality of activation of the emitter described above does not enable images of the anatomical part to be obtained having a definition sufficient for the capacities of the average operator.

SUMMARY OF THE INVENTION

The aim of the present invention is to provide a method for activation of an emitter of a computed tomography scanner and a computed tomography scanner implementing said method that will enable the drawback described above to be overcome and, at the same time, will be easy and inexpensive to implement. According to the present invention a method for activation of an emitter of a computed tomography scanner and a computed tomography scanner are provided as claimed in the attached Claims.

BRIEF DESCRIPTION OF THE DRAWINGS

For a better understanding of the present invention, a preferred embodiment is now described, purely by way of non-limiting example and with reference to the attached plates of drawings, wherein.

DETAILED DESCRIPTION OF THE INVENTION

Figure 1:
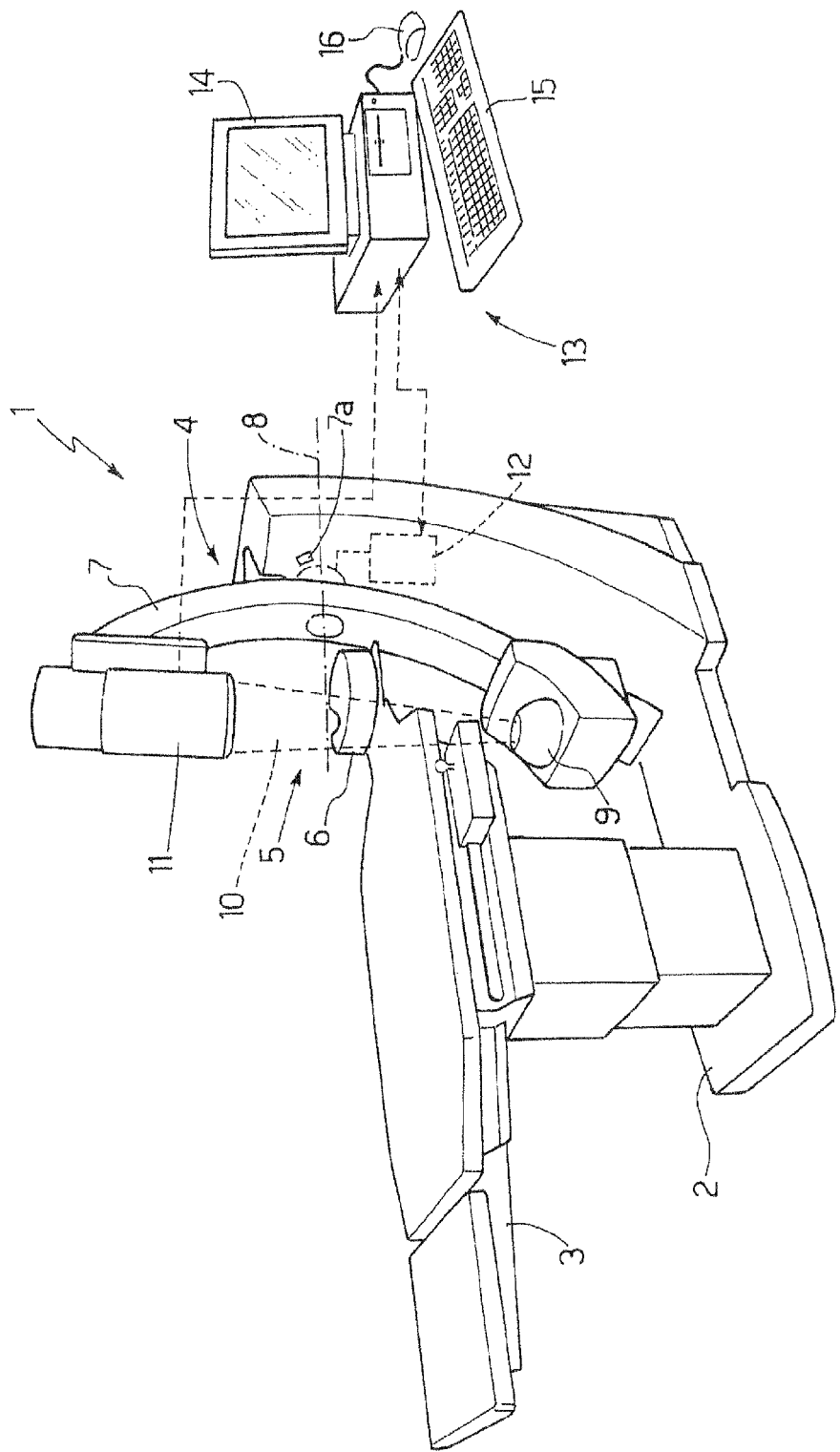
FIG. 1 illustrates a computed tomography scanner of the type used in dentistry, and in particular a cone-beam computed tomography scanner.

In FIG. 1, designated as a whole by 1 is a cone-beam computed tomography scanner comprising a frame 2, a couch 3 for supporting a patient (not illustrated) lying down, and an x-ray source-detector assembly 4 designed to rotate about an area of analysis 5 located in a region corresponding to a headrest 6 of the couch 3 for acquiring a plurality of radiographies of a part of the patient's head, for example a maxillofacial complex such as the dental arches, the mandibular bone, the maxillary bone of the patient, or else an anatomical region, such as a condyle of the mandible. For reasons of simplicity and generalization, hereinafter the patient's head will be referred to as "body under analysis" and the particular anatomical part will be referred to as "object to be analysed".

The source-detector assembly 4 comprises: a rotating support constituted by an arm 7, mounted on the frame 2 and motor-driven so as to rotate about a substantially horizontal axis 8 of rotation traversing the region of analysis 5; a position sensor 7a for detecting the angular position of the arm 7 with respect to the axis 8; an x-ray emitter 9, mounted on a first end of the arm 7 and facing in the direction of the axis 8 for emitting a conical beam 10 of x-rays towards the area of analysis 5; and an x-ray detector 11, mounted on the opposite end of the arm 7 and facing in the direction of the axis 8 for receiving the beam 10 after it has traversed the area of analysis 5 so as to be able to acquire a plurality of radiographies of the dental arches during a single rotation of the arm along an angular path of less than or equal to 360°.

The tomography scanner 1 further comprises a control unit 12, connected to the source-detector assembly 4 for controlling emission and reception of the beam 10 in a way synchronous with rotation of the arm 7, a processing unit 13 connected to the detector 11, for receiving, storing, and processing the radiographies so as to reconstruct images of the object, and to the control unit 12 for activating the source-detector assembly 4 on the basis of commands imparted by an operator or of instructions with which the processing unit 13 itself is programmed. The processing unit 13 is constituted, for example, by a personal computer provided with a monitor 14 for displaying the reconstructed image, and a keyboard 15, and a mouse 16 for acquiring data supplied and/or commands imparted by the operator.

Figure 2:
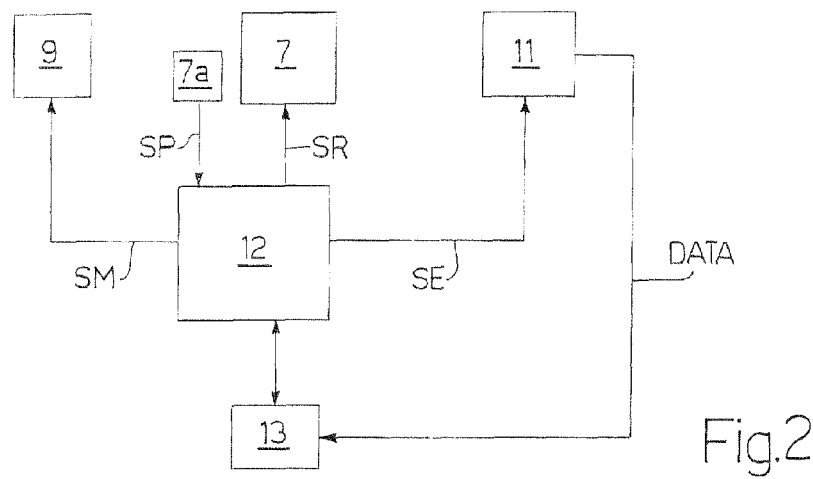
FIG. 2 illustrates a block diagram that describes the signals involved between some units of the computed tomography scanner of FIG. 1.

With reference to FIG. 2, the control unit 12 is configured for supplying a command signal SR to the motor-driven arm 7, a command signal SM to the emitter 9 and a command signal SE to the detector 11, said command signals SR, SM and SE being synchronised with respect to one another for enabling acquisition of radiographies for different angular positions of the arm 7.

The detector 11 is designed to supply the radiographies acquired, designated by DATA, to the processing unit 13, and the position sensor 7a is designed to supply a position signal SP that informs the control unit 12 on the angular position reached by the arm 7.

The command signal SR produces a succession of rotations of the arm 7 about the axis 8 according to a given angular step. The succession of rotations rotates the arm 7 along a series of angular positions $\alpha i$, the index "i" of which assumes integer values between 1 and N, comprised between an initial angular positional and a final angular position $\alpha N$ determined according to the type of analysis to be made and defining said angular path described by the arm 7.

Figure 3:
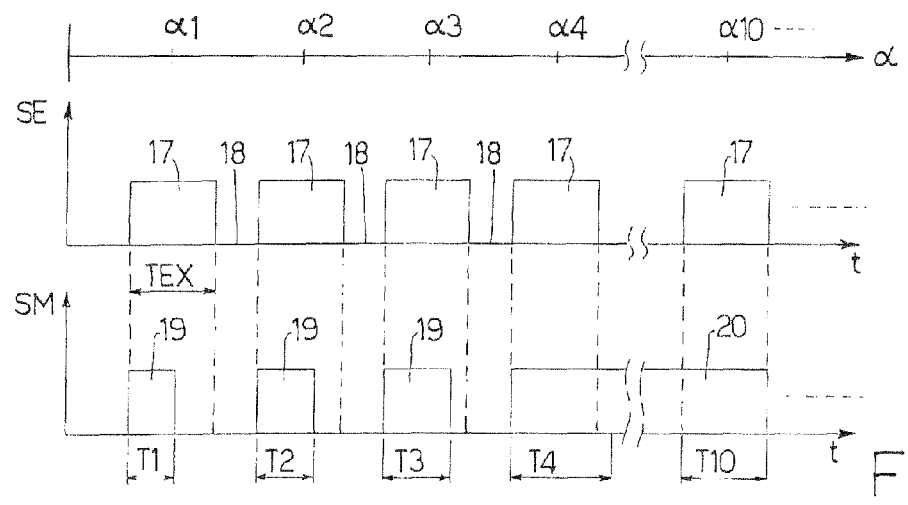
FIGS. 3 and 4 illustrate waveforms of some of the signals indicated in FIG. 2 according to two different embodiments of the present invention.

With reference to FIG. 3, the command signal SE comprises a succession of activation pulses 17, during which the detector 11 is activated, i.e., it is ready for acquisition of respective radiographies, in alternation with periods of de-activation 18, during which the detector 11 does not acquire any radiography in so far as it transfers the radiographies acquired (DATA) to the processing unit 13. The activation pulses 17 each have a duration equal to a given exposure interval TEX characteristic of the detector 11. The duration of the exposure interval TEX is optionally configurable via the processing unit 13. Each activation pulse 17 is generated in a respective angular position $\alpha i$ for acquiring a radiography of the body under analysis corresponding to said angular position $\alpha i$.

The method for activation of an emitter of a computed tomography scanner according to the present invention envisages generating a command signal SM for the emitter 9 as described hereinafter.

The command signal SM comprises a succession of emission pulses 19, each of which activates the emitter 9 for emitting said beam 10 according to a corresponding x-ray pulse (not illustrated). The rising edge of each emission pulse 19 is synchronised on the rising edge of a respective activation pulse 17, as illustrated in FIG. 3, in such a way that the emitter 9 emits an x-ray pulse only when the detector 11 is ready for acquisition of a radiography.

Each emission pulse 19 has the same amplitude to control emission of x-ray pulses having the same intensity. The duration of each emission pulse 19 hence determines the radiation dose supplied by the corresponding x-ray pulse. Associated to each angular position $\alpha i$ is a duration Ti of emission of the beam 10, which defines a corresponding radiation dose required in that angular position $\alpha i$ according to a given criterion. Hence, associated to each angular position $\alpha i$ is in principle an emission pulse 19 presenting a duration Ti.

However, the command signal SM envisages an emission pulse 19 in each angular position $\alpha i$ only if the corresponding duration Ti is shorter than or equal to the exposure interval TEX; otherwise, the command signal SM remains high to leave the emitter 9 turned on until the arm 7 reaches an angular position $\alpha i$, associated to which is a duration Ti once again shorter than or equal to the exposure interval TEX. In other words, a number of emission pulses 19 are united to form a longer single pulse, designated by 20, so as to prevent useless transients of turning-on and turning-off of the emitter 9 during periods of de-activation 18. The duration of said pulse 20 is substantially equal to the sum of the consecutive durations Ti that are individually greater than the exposure interval TEX.

FIG. 3 illustrates an example in which the command signal SM comprises three emission pulses 19 of respective durations T1, T2 and T3 shorter than the exposure interval TEX and a subsequent period at high level, starting from the angular position $\alpha 4$, associated to which is the duration T4 longer than the exposure interval TEX, up to the angular position $\alpha 10$, associated to which is the duration T10 equal to the exposure interval TEX.

As regards the criterion of association between the angular positions $\alpha i$ and the durations Ti, the distribution of the durations Ti along the succession of angular positions $\alpha i$ is calculated by the processing unit 13 as a function of the dimensions of the body under analysis, of the type of object to be analysed, and of the position of the object within the body under analysis.

In greater detail, there is determined a distribution of coefficients $\beta i$ representing the durations, normalized to a minimum value and/or maximum value thereof, of the x-ray pulses necessary for acquiring radiographies of the type of object to be analysed positioned in a certain way in the body under analysis. The dimensions of the body under analysis are estimated by means of one or two scout-view acquisitions of the body itself. On the basis of the dimensions estimated, there is determined a minimum value Tmin and/or a maximum value Tmax that a generic duration Ti must assume to define a minimum and/or maximum radiation dose. By combining the distribution of coefficients $\beta i$ with the minimum value Tmin and/or maximum value Tmax, the desired durations Ti are obtained.

The distribution of coefficients $\beta i$ is hence pre-defined, in so far as it is necessary to know a priori the type and position of the object to be analysed. Once a plurality of types of object that it is desired to analyse within the body is known, it is possible to pre-calculate off line a corresponding plurality of distributions of coefficients $\beta i$ and store said plurality of distributions of coefficients $\beta i$ in an internal memory of the processing unit 13. Consequently, before acquiring the radiographies for the reconstruction of the images, the operator must select the distribution of coefficients $\beta i$ from among a plurality of distributions of coefficients $\beta i$ stored in the processing unit 13.

In the field of dentistry, for example, it is necessary to calculate off line and store in the processing unit 13 distributions of coefficients $\beta i$ of various anatomical parts of the skull starting from the known proportions of a generic skull.

In the case where it is desired to analyse a particular anatomical part, for example the right condyle of the mandible, the operator selects the distributions of coefficients $\beta i$ corresponding to the right condyle of the mandible. Then, before acquiring the radiographies necessary for reconstruction of the images of the right condyle of the mandible, the operator issues a command to the tomography scanner 1 to acquire a first latero-lateral scout-view and a second antero-posterior scout-view of the patient's head. From the scout-views, the processing unit 13 estimates the dimensions of the skull and hence the thickness of the bony parts. On the basis of the dimensions estimated, the processing unit 13 calculates the minimum value Tmin and/or maximum value Tmax of the durations Ti. Next, the processing unit 13 calculates the distribution of the durations Ti combining the distribution of coefficients $\beta i$ selected with the minimum value Tmin and/or the maximum value Tmax.

At this point, the tomography scanner 1 can carry out the cycle of acquisition of radiographies, by rotating the arm 7 along the angular path defined between the angular positions $\alpha 1$ and $\alpha N$ and controlling the emitter 9 with the succession of emission pulses 19 having the durations Ti calculated as described above.

Figure 4:
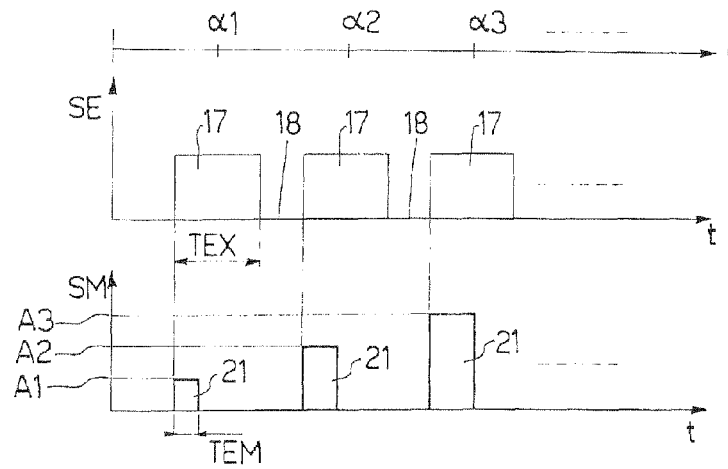

According to a second embodiment illustrated in FIG. 4, the command signal SM comprises a succession of emission pulses 21, each of which activates the emitter 9 for emitting said beam 10 according to an x-ray pulse that supplies a dose of radiation associated to the respective angular position $\alpha i$. Each radiation dose is defined, keeping constant the duration of the emission pulses 19 at a value TEM and acting on their amplitude Ai to vary the intensity of the corresponding x-ray pulses. In this way, the need to modify the command signal SM in relation to the exposure interval TEX is avoided, as illustrated in FIG. 3.

The further differences with respect to the embodiment illustrated by FIG. 3 are described in what follows. On the basis of the dimensions estimated via the scout-views, the processing unit 13 calculates the minimum value Amin and/or maximum value Amax of the amplitude Ai. In addition, on the basis of the same type of object to be analysed and of its position in the body, there is determined a distribution of coefficients $\delta i$ that represent the amplitudes, normalized to a minimum value and/or maximum value thereof, of the emission pulses 21 necessary for acquisition of radiographies of the type of object to be analysed positioned in a certain way in the body under analysis.

According to a third embodiment (not illustrated), each radiation dose is defined via a pair of values (Ti, Ai) of duration and amplitude of the emission pulses, calculation of which is carried out in a way that can be inferred from what has been described for the previous embodiments.

In a fourth embodiment (not illustrated), the detector 11 is configured for generating itself the command signal SE and for supplying said signal to the control unit 12 as soon as the detector 11 itself is electrically supplied. The control unit 12 receives the command signal SE and converts said signal into the command signal SM, which has the same information content as the command signal SE; i.e., it comprises a succession of emission pulses 19 for activation of the emitter 9, each of which is synchronised with the rising edge of a corresponding activation pulse 17 generated by the detector 11, but has a different format and/or waveform with respect to the command signal SE so as to be usable directly by the emitter 9. In other words, the detector 11 is configured for generating autonomously the command signal SE, which controls directly the emitter 9 in the form of the command signal SM. In particular, the command signal SM is generated with a waveform according to any one of the embodiments described previously.

From the above description, it emerges that the method for activation of an emitter of a computed tomography scanner according to the present invention is applicable to any tomography scanner using an emitter that emits a conical x-ray beam for acquiring images of any anatomical part of the human body or of a particular part of a body or generic object positioned in the area of analysis of the tomography scanner.

The main advantage of the method for activation of an emitter of a tomography scanner is that of enabling images of anatomical parts of a human body to be obtained rapidly and in a substantially automatic way, said images being well defined to the eye of the average operator.

The invention claimed is:

1. A method for activation of an emitter of a computed tomography scanner comprising a detector designed to receive an X-ray beam emitted by the emitter through an object to be analysed, and rotating supporting means, which are designed to support and rotate the emitter and the detector about said object; the method comprising:
  rotating the supporting means along a series of angular positions ($\alpha i$);
  generating a succession of first pulses, each of which activates the detector in a respective angular position ($\alpha i$) for acquiring a respective radiography of the object; and
  generating a succession of second pulses for activating the emitter in order to emit a radiation dose in each angular position ($\alpha i$);
  associating with each angular position ($\alpha i$) a respective radiation dose in such a way as to pre-define a distribution of radiation doses along the series of angular positions ($\alpha i$);
  defining each said radiation dose by at least one parameter associated to the respective angular position ($\alpha i$) so as to form said distribution of radiation doses;
  the method being characterized in that each said parameter is constituted by a duration of emission (Ti) of said x-ray beam associated with the respective angular position ($\alpha i$), in that each of the first pulses has one and the same duration of emission (Ti) that is longer than the duration of exposure (TEX), and in that generating a succession of second pulses comprises:
  in the case of consecutive durations of emission (Ti) that are longer than the duration of exposure (TEX), generating just one second pulse is the angular positions ($\alpha i$) associated with said durations of emission (Ti), said single second pulse being long to the extent that it leaves the emitter activated until said supporting means reach an angular position ($\alpha i$) associated to which is a duration (Ti) that is shorter than or equal to the exposure interval (TEX).

2. The method according to claim 1, in which said object to be analysed is a portion of a body traversed by said X-ray beam; said distribution of radiation doses is calculated as a function of the dimensions of the body, of the type of object, and of the position of the object in the body.

3. The method according to claim 2, comprising:
  pre-calculating a distribution of coefficients that expresses said distribution of parameters normalized to a first value of said parameter corresponding to which is a maximum and/or minimum radiation dose for said type of object in said position in the body;
  said distribution of parameters being calculated as a function of the distribution of coefficients.

4. The method according to claim 3, comprising:
  acquiring at least one scout-view of said body for estimating the dimensions of the body itself; and
  calculating a second value of said parameter as a function of the dimensions estimated, there corresponding to said second value a minimum and/or maximum radiation dose for those dimensions;
  said distribution of parameters being calculated by combining said distribution of coefficients with the second value.

5. The method according to claim 1, in which each of said first pulses has one and the same duration of exposure (TEX); generating a succession of second pulses comprising:
  in the case of a duration of emission (Ti) shorter than or equal to the duration of exposure (TEX), generating respective second pulses in the angular positions ($\alpha i$), associated with said durations of emission (Ti), each second pulse presenting a duration equal to the respective duration of emission (Ti).

6. The method according to claim 1, in which the second pulse-has a duration substantially equal to the sums of said consecutive durations of emission (Ti).

7. The method according to claim 1, in which said succession of first pulses is generated by said detector.

8. The method according to claim 7, in which said succession of second pulses is generated so that each second pulse (19, 20) is synchronised on the rising edge of a corresponding said first pulse.

9. A computed tomography scanner comprising: an emitter for emitting an X-ray beam through an object to be analysed; a detector designed to receive said X-ray beam after the X-ray beam has traversed the object; rotating supporting means, which are designed to support and rotate the emitter and the detector about said object; and control and processing means, which are designed to generate command pulses for the detector and the emitter such as to synchronise emission and reception of the X-ray beam with rotation of the supporting means for acquiring radiographies of the object and to process said radiographies for reconstructing images of the object; the computed tomography scanner being characterized in that said control and processing means are configured for implementing the method for activation of an emitter of a computed tomography scanner according to claim 1.

10. A computed tomography scanner for use in dentistry built according to claim 9.

11. The method according to claim 1, in which each radiation dose is defined by a pair of parameters associated with the respective angular position ($\alpha i$); the pair of parameters being constituted by said duration of emission (Ti) and by the amplitude (Ai) of the respective second pulse.

* * * * *